United States Patent
Campbell et al.

(10) Patent No.: US 11,624,691 B2
(45) Date of Patent: Apr. 11, 2023

(54) SYSTEMS AND METHODS FOR WATER CONTENT MEASUREMENT CORRECTION

(71) Applicant: ADDIUM, INC., Pullman, WA (US)

(72) Inventors: Scott H. Campbell, Pullman, WA (US); Gregory M. Kelley, Pullman, WA (US); Gaylon S. Campbell, Pullman, WA (US); Timothy G. Mumford, Pullman, WA (US)

(73) Assignee: ADDIUM, INC., Pullman, WA (US)

( * ) Notice: Subject to any disclaimer, the term of this patent is extended or adjusted under 35 U.S.C. 154(b) by 185 days.

(21) Appl. No.: 16/950,733

(22) Filed: Nov. 17, 2020

(65) Prior Publication Data
US 2022/0155198 A1 May 19, 2022

(51) Int. Cl.
*G01N 5/04* (2006.01)
*F26B 25/06* (2006.01)
*G01N 33/02* (2006.01)

(52) U.S. Cl.
CPC ........... *G01N 5/045* (2013.01); *F26B 25/06* (2013.01); *G01N 33/02* (2013.01); *F26B 2210/00* (2013.01)

(58) Field of Classification Search
CPC ..... F26B 25/06; F26B 2210/00; G01N 5/045; G01N 33/02
USPC .......................................................... 34/427
See application file for complete search history.

(56) References Cited

U.S. PATENT DOCUMENTS

| | | | | |
|---|---|---|---|---|
| 5,275,957 A * | 1/1994 | Blades | ............... | G01N 33/1846 422/78 |
| 6,616,330 B2 * | 9/2003 | Nakamura | ............. | G01N 5/045 374/31 |
| 8,991,067 B2 * | 3/2015 | Zielinski | ................... | F26B 5/04 34/403 |
| 10,199,635 B2 * | 2/2019 | Ho | ............................. | F26B 7/00 |
| 10,876,792 B2 * | 12/2020 | Zielinski | ................ | F26B 9/106 |
| 11,287,185 B1 * | 3/2022 | Jiang | ......................... | F26B 5/06 |
| 11,408,679 B2 * | 8/2022 | Ohnari | .................... | F26B 21/06 |
| 2016/0229706 A1 * | 8/2016 | Ackerman | ................ | C02F 1/16 |
| 2022/0097044 A1 * | 3/2022 | Babcock | ................ | G01N 33/02 |
| 2022/0155198 A1 * | 5/2022 | Campbell | ................ | F26B 3/04 |

FOREIGN PATENT DOCUMENTS

| | | | |
|---|---|---|---|
| DE | 10153894 A1 * | 7/2002 | ......... G01N 25/4866 |
| JP | 2002148230 A * | 5/2002 | ......... G01N 25/4866 |
| WO | WO-2013116599 A1 * | 8/2013 | ............. F26B 21/08 |

OTHER PUBLICATIONS

De Knegt, R. J., et al., "Improvement of the Drying Oven Method for the Determination of the Moisture Content of Milk Powder", Aug. 27, 1998, 733-738.

* cited by examiner

*Primary Examiner* — Stephen M Gravini

(74) *Attorney, Agent, or Firm* — Dorsey & Whitney LLP

(57) ABSTRACT

Methods and systems for correction of water content measurements include determining an apparent water content measurement of a sample material while the sample material is dried in ambient vapor pressure conditions, determining a correction value that represents a relationship between the apparent water content and the vapor pressure, and correcting the apparent water content measurement based on the correction value. These methods and systems can reduce cost, measurement time, and error in water content measurement for products that lose water over time, such as while being dried or cured.

19 Claims, 4 Drawing Sheets

SYSTEMS AND METHODS FOR WATER CONTENT MEASUREMENT CORRECTION

TECHNICAL FIELD

The present disclosure relates to systems and methods for measuring water content in samples of food products, particularly within short timeframes and in settings where there is no control of the drying oven environment.

BACKGROUND

The amount of water within food products is carefully monitored and controlled. Water content of food products is often a major component of the weight of the products, and these products are often sold by weight and with mandated minimum water content. Accordingly, producers and factory operators in the food industry require reliable water content measurements of their products at key points in manufacturing processes, such as just before they are packaged and shipped to clients or customers. Thus, these measurements are made both to control and adjust processes and to satisfy legal requirements.

Water content measurements are typically made by weighing a sample, drying it in an oven, and weighing the sample again after drying. The water content can thereby be calculated as the weight loss divided by the post-drying weight of the product. In other words, the product is dried in the oven until little or no evaporation occurs, and then the difference in the weight of the wet and dry product is determined to be the weight of the water evaporated in the drying process. The accuracy of those measurements is influenced by a number of factors, which, typically, are not well controlled. For this and other reasons, there is a constant need for improvements to measurement and monitoring of water content in food production systems and methods.

SUMMARY

One aspect of the present disclosure relates to a system for determining water content of a product. The system can include a drying device to dry a sample of a product in a drying chamber, a vapor pressure sensor to measure a vapor pressure in air at the drying device, a weighing device to measure weight of the product in the drying chamber, and a computing device having a processor and a memory device having instructions encoded thereon. When executed by the processor, the instructions can cause the processor to obtain an apparent water content of the sample based on a weight difference of the sample obtained via the weighing device and based on the vapor pressure in air at the drying device obtained via the vapor pressure sensor, determine a correction value representing a change in apparent water content relative to testing environment vapor pressure, and modify the apparent water content measurement by applying the correction value to the apparent water content.

In some embodiments, obtaining the apparent water content can comprise: obtaining a first weight of the sample in the drying chamber at a first time using the weighing device, measuring the vapor pressure in air at the drying device using the vapor pressure sensor, drying the sample in the drying chamber using the drying device, obtaining a second weight of the sample in the drying chamber at a second time using the weighing device, determining a weight difference between the first and second weights of the sample, and calculating an apparent water content of the sample based on the weight difference and the vapor pressure in air at the drying device.

In some configurations, the method can further comprise measuring equilibrated water content values of the sample at multiple relative humidities, measuring vapor pressures at the multiple relative humidities, and calculating a mathematical relationship between the equilibrated water content values and the vapor pressures, wherein the correction value comprises a slope of the mathematical relationship.

Applying the correction value to the apparent water content can comprise taking a difference between the apparent water content measurement and a product of the correction value and the vapor pressure in air at the drying device. The computing device can be configured to access a database of correction values comprising a predetermined correction value for the product. The computing device can also be configured to access a database of correction values comprising a second correction value for a second product having a characteristic in common with the product and to use the second correction value as the correction value for the product. In some embodiments, the sample is a food sample, wherein the drying device is configured to dry the food product.

Another aspect of the disclosure relates to a method for correcting a water content measurement of a product, which can comprise obtaining an apparent water content measurement of a product at an ambient vapor pressure in air at a testing environment, determining a correction value representing a change in apparent water content relative to testing environment vapor pressure, and modifying the apparent water content measurement by taking a difference between the apparent water content measurement and a product of the correction value and the ambient vapor pressure.

In some embodiments, the ambient vapor pressure is within a range extending from about 0.5 kPa to about 6.0 kPa. Obtaining the water content measurement can comprise drying the product. The testing environment can be an oven, wherein drying the product can comprise heating the product in the oven, and the testing environment vapor pressure can be a vapor pressure in the oven. In some embodiments, determining the correction value can comprise accessing a database of correction values comprising a predetermined correction value for the product. Determining the correction value can comprise accessing a database of correction values comprising a second correction value for a second product having a characteristic in common with the product and using the second correction value for the correction value of the product. Determining the correction value can comprise measuring equilibrated water content values of the product at multiple relative humidities in a controlled-humidity instrument and calculating a linear relationship between the equilibrated water content values and vapor pressures corresponding to each of the equilibrated water content values, wherein the correction value comprises a slope of the linear relationship. The method can further comprise reducing the ambient vapor pressure by a vapor pressure standard value.

Yet another aspect of the disclosure relates to a non-transitory computer-readable medium comprising instructions encoded thereon which, when executed by a processor, cause the processor to perform a method including obtaining an apparent water content measurement of a sample product based on a weight difference of the sample while the sample is dried in a testing environment, measuring a vapor pressure in the testing environment, determining a correction value representing a relationship between the apparent water content and the vapor pressure, and correcting the apparent water content measurement by reducing the apparent water content measurement by a factor dependent upon the correction value and the vapor pressure in the testing environment.

In some embodiments, the factor is a product of the correction value and the vapor pressure in the testing environment. Additionally, determining the correction value can comprise accessing a database of correction values and identifying a correction value correlating to a property of the sample product. The correction value can represent a change in apparent water content based on vapor pressure for the sample material.

The above summary is not intended to describe each embodiment or every potential implementation of the subject systems and methods. The Figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the embodiments of the present disclosure may be realized by reference to the following drawings. In the appended figures, similar components or features may have the same reference label.

Figure 1:
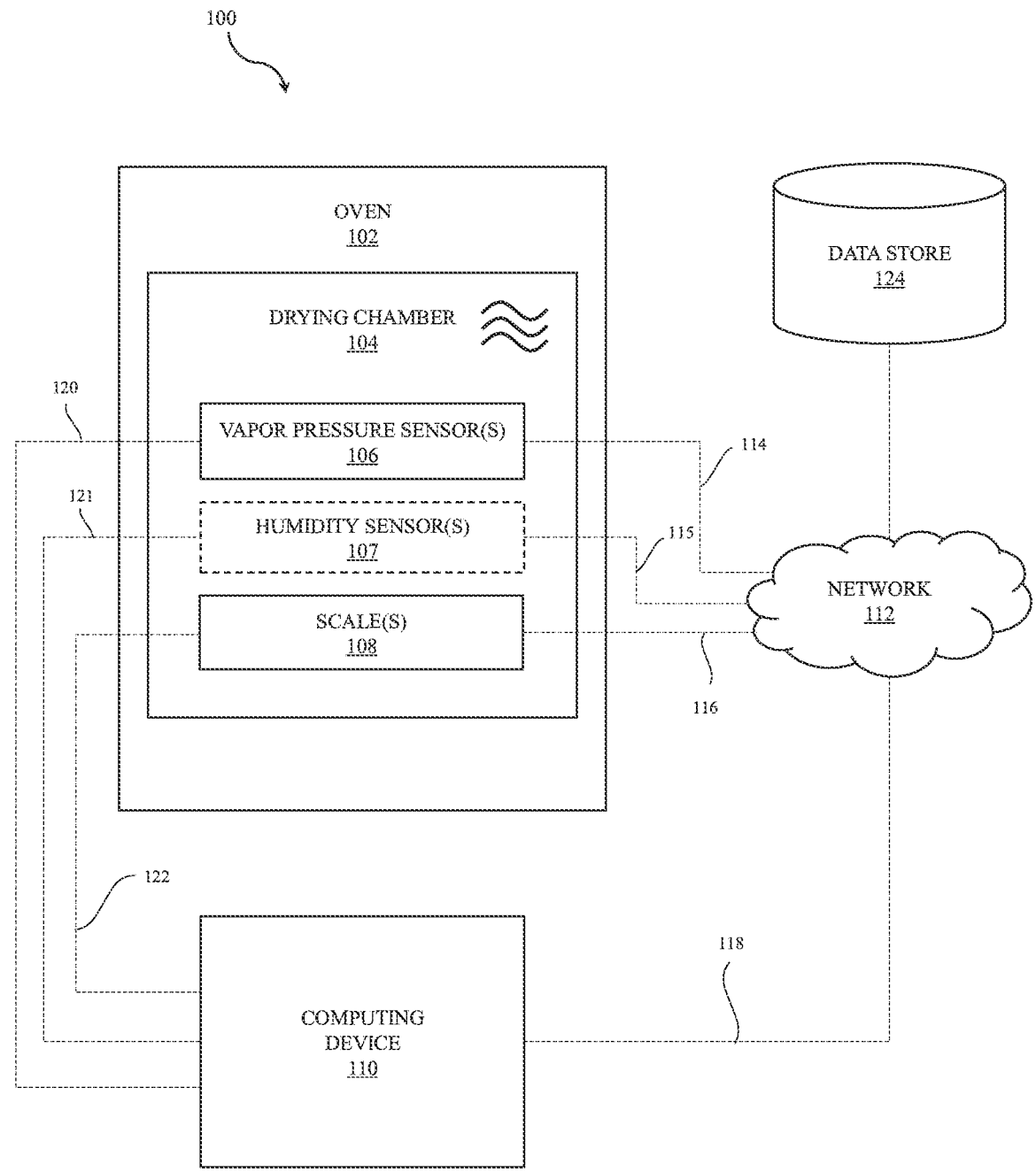
FIG. 1 is a block diagram of a system for determining water content of a product.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

It is difficult for manufacturers to account for variable humidity of air in an oven or other drying environment while measuring water content of the product being dried. As the humidity of air in the oven increases, the apparent water content of the sample decreases. For example, the humidity of the air inside or outside the oven can change with the weather or as seasons change. Also, water evaporating from the food product during the drying process can affect the water vapor pressure of air in the oven. A product being dried in an oven with high relative humidity will appear to have lower water content (based on a pure weight measurement) than an identical product being dried in an oven with low relative humidity due to the amount of drying possible in the second case enabling the product to reduce its weight more via evaporation.

In order to combat this issue, in high accuracy drying ovens, dry nitrogen, or desiccated air can be supplied to the oven to control its humidity, or a vacuum can be applied. However, these procedures are expensive to use and operate. Thus, most drying ovens use ambient air, which varies widely in humidity and vapor pressure. This results in variation in the water content measurement from one drying time to the next (e.g., each hour, each week, each season, etc.).

When oven-drying a food sample, the oven dries the sample until the vapor pressure of the sample is equal to the vapor pressure of the oven. As the vapor pressure of the oven increases, so does the vapor pressure of the sample. The vapor pressure of the sample can be calculated as the product of the sample water activity and the saturation vapor pressure at oven temperature. An increase in oven vapor pressure results in an increase in sample water activity, and therefore of sample water content. For accurate water content measurements, it is therefore necessary to specify the oven conditions (temperature and vapor pressure) to which the sample will be dried. This effect is typically small but is significant enough to be measured with good laboratory techniques, introducing unacceptable measurement error. The additional equipment required to control the sample environment adds substantially to the cost and complexity of the measurement.

Accordingly, by using systems and methods of the present disclosure, water content measurements can be made without needing expensive additional equipment and the labor and time related to using it to obtain correct water content measurements. Water content measurements obtained from a standard drying apparatus (e.g., an oven) can be obtained and then corrected based on the surrounding relative humidity to obtain a final water content measurement very similar to a measurement obtained from using controlled-humidity drying equipment.

The effect of humidity on water content measurement error depends on the sample being measured, so both the oven humidity and the kind of product being dried need to be known to correct a measurement in an uncontrolled-humidity environment. Embodiments of the present disclosure include systems and methods for making correct moisture measurements when oven humidity varies based on knowing what product is being measured, accessing a database of products via a computer network to obtain a correction factor for the product being analyzed, determining the humidity of the oven air, and correcting the final moisture reading to find the moisture content at a standard state—as if a controlled-humidity oven or vacuum oven were being used.

The present description provides examples, and is not limiting of the scope, applicability, or configuration set forth in the claims. Thus, it will be understood that changes may be made in the function and arrangement of the elements discussed herein without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

FIG. 1 shows an embodiment of the present disclosure including a system 100 for determining water content of a product that comprises an oven 102 or other drying device to dry a sample of a product in a drying chamber 104 (e.g., a heated chamber within the oven), a vapor pressure sensor 106 to measure a vapor pressure of water in air at the drying device (e.g., a vapor pressure sensor in fluid communication with the drying chamber 104), an optional humidity sensor 107 (e.g., a sensor for measuring relative humidity in the drying chamber 104, which is shown in broken lines to indicate its optional nature), a scale 108 or other weighing device (e.g., a balance or load cell) or sensor to measure weight of the product in the drying chamber, and a computing device 110 connected to at least the sensors 106, 108. The computing device 110 can be in electrical communication with the sensors 106, 107, 108 via an electronic communications network 112 (as indicated by wired or wireless electronic communication paths 114, 115, 116, and 118) or directly (as indicated by wired or wireless electronic communication paths 120, 121, 122). Accordingly, sensor signals can be obtained by the computing device 110 being directly connected to the sensors 106, 107, 108 or by signals routed to the computing device 110 via a network 112. Additionally, the computing device 110 can be connected to a data store directly (e.g., a memory device that is part of the computing device 110) or via a network 112 (e.g., data store 124 or via another computing device in the network 112 having the data store 124). The sensor signals and associated data can be tracked by the computing device 110 over time, and the computing device 110 can access data of the data store 124 to convert water content measurements of a sample food product in the drying chamber 104—that are taken in the uncontrolled-humidity drying chamber 104—into corrected water content measurements that reflect the water content of the product that would be obtained using slower, more expensive controlled-humidity equipment.

The computing device can include a processor and a memory device having instructions encoded thereon. See FIG. 6 and its related descriptions herein. When executed by the processor, the instructions can implement a method for measuring and correcting water content that comprises obtaining an apparent water content of the sample based on a weight difference of the sample as it dries and based on the vapor pressure of water in air at the drying device, determining a correction value representing a change in apparent water content relative to testing environment vapor pressure of water, and modifying the apparent water content measurement by taking a difference between the apparent water content measurement and a product of the correction value and the vapor pressure of water in air at the drying device. Methods of obtaining the apparent water content of the sample based on a weight difference and vapor pressure in air at the drying device, determining the correction value, and modifying the apparent water content measurement are discussed in greater detail below. See FIG. 3.

In an example embodiment, the sample vapor pressure ($e_s$) can be determined by Equation 1:

$$e_s = a_w e_o(T_s), \qquad \text{(Equation 1)}$$

wherein $a_w$ is the water activity of the drying sample, and $e_o(T_s)$ is the saturation vapor pressure at sample (and oven) temperature. In various embodiments, the drying sample can include one or more food products (e.g., a baked food, jerky, kibble, other food products described herein, related products, and combinations thereof), leather and cured materials, pharmaceutical products, plant products (e.g., hemp or biofuels), soils, or similar products having wetness or moisture content or that are subject to drying.

If ambient air is being circulated through the oven, the vapor pressure of the ambient air in the oven ($e_a$) can be calculated from Equation 2:

$$e_a = h_r e_o(T_a), \qquad \text{(Equation 2)}$$

where $h_r$ is the room humidity and $e_o(T_a)$ is the saturation vapor pressure at air temperature. When the sample is oven dry, i.e., vapor pressure equilibrium between the air and the sample is reached, $e_s$ equals $e_a$ or Equation 1 is equal to Equation 2. Accordingly, Equations 1 and 2 can be combined and rearranged to give Equation 3, which indicates the water activity of the drying sample:

$$a_w = h_r \frac{e_0(T_a)}{e_0(T_s)}. \qquad \text{(Equation 3)}$$

Figure 2:
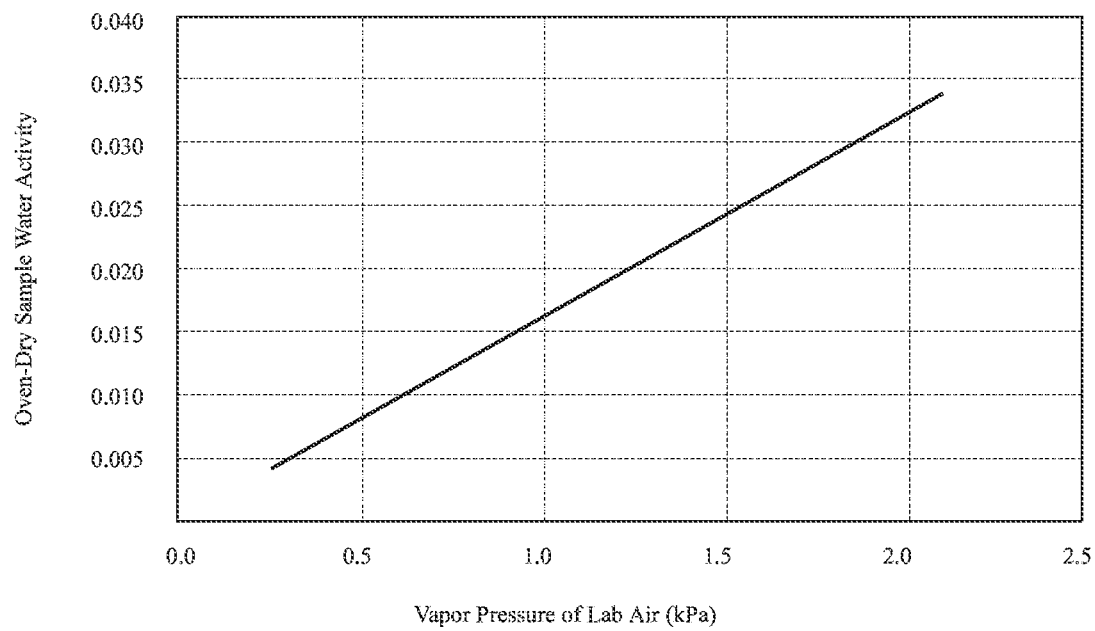
FIG. 2 is a chart showing example water activity measurements relative to laboratory vapor pressure.

If the oven temperature is 100 degrees Celsius, and the laboratory temperature is 22 degrees Celsius, then the relationship between lab vapor pressure and dry sample water activity is shown in the example chart of FIG. 2. Over the range of vapor pressures that might exist in the lab (e.g., between about 0.25 kPa and about 1.55 kPa), the dry sample water activity could vary by an order of magnitude (e.g., from about 0.0025 to about 0.025). Accordingly, using only an ambient air drying process can result in large variations in the measured sample water activity. FIG. 2 also shows that a substantially linear relationship exists between the water activity of the sample material and the vapor pressure of the lab air under these conditions.

Figure 3:
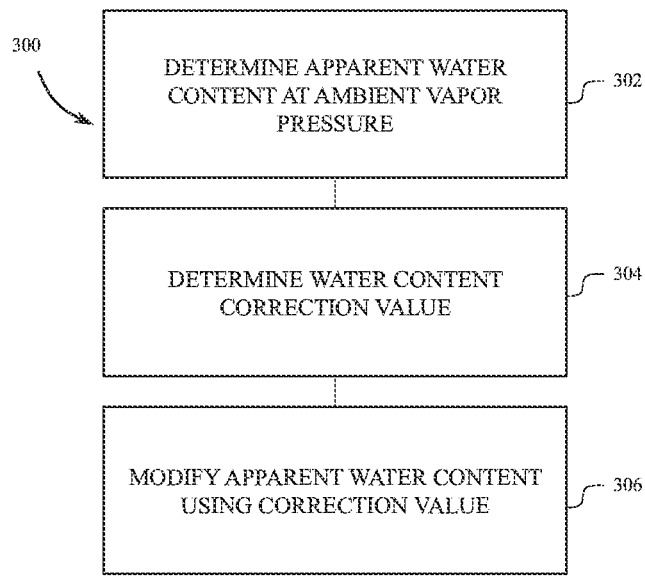
FIG. 3 is a flow diagram showing actions for modifying apparent water content measurements of a sample.

FIG. 3 illustrates a flow diagram showing a method 300 by which water content measurements of a sample material that are gathered at ambient humidity conditions can be corrected to reflect water content measurements gathered as if the sample material was in a controlled-humidity or zero humidity testing environment. The method 300 can include obtaining, calculating, and/or determining an apparent water content measurement of the sample material or product sample at an ambient vapor pressure (e.g., at the vapor pressure of water in air at a testing environment), as indicated in block 302. The apparent water content measurement can be determined by weighing the sample before starting a test (or otherwise obtaining a pre-drying weight of the sample), drying the sample under ambient vapor pressure conditions (e.g., in an oven such as oven 102 and with the ambient vapor pressure of water present in the oven or its surroundings), and obtaining a post-drying weight of the sample when it reaches vapor pressure equilibrium with the drying chamber (e.g., 104) under ambient conditions. In this way, the apparent or pre-corrected water content (i.e., the amount of water weight in the product relative to its remaining non-water weight under the ambient conditions) can be determined by calculating the difference between the pre-drying weight and the post-drying weight of the product. Thus, that difference represents the water weight lost from the sample while drying in the oven or other drying chamber.

The method 300 can also include determining a water content correction value, as shown in block 304. In some embodiments, a controlled temperature and controlled humidity drying device can be used to determine a water content correction value. The device can comprise a sealable enclosure and can remove moisture from air that is used to dry the sample product or to remove traces of water from a substantially dry sample. A controlled-humidity drying device can be used to determine water content of a sample product at different ambient relative humidity levels, and those water content measurements can be used to derive a water content correction value. In some embodiments, a controlled-temperature device can be positioned within a controlled-humidity chamber of another device, or vice versa, for the same effect.

In an example embodiment, at least one material sample can be positioned in a controlled vapor pressure and temperature environment, and the sample(s) can be dried at various humidity levels for equal time periods. For instance, in one embodiment, the samples can be dried at an ambient humidity of 80% for an initial period of 2, 4, or 8 hours (or another initial period time duration), then the samples can be dried at an ambient humidity of 60% for an additional 1, 2, or 4 hours, then at 40% humidity for another 1, 2, or 4 hours and at 20% humidity for yet another 1, 2, or 4 hours (or at other additional period time durations). Weights of the samples can be tracked over the entire time period to determine water content measurements based on the ambient humidity levels at each humidity state.

Figure 4:
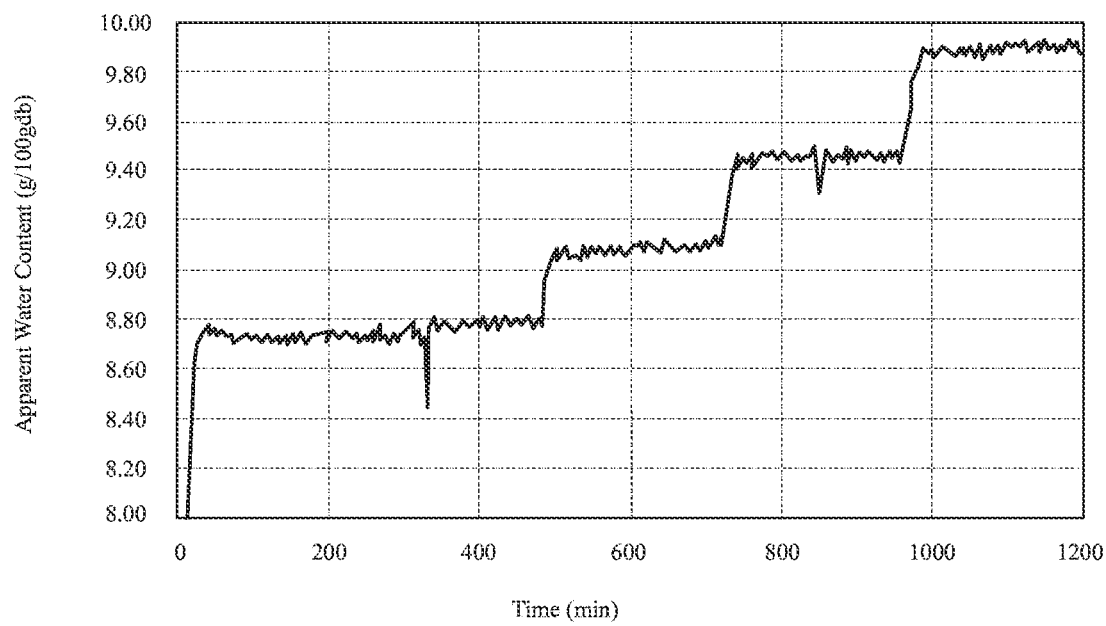
FIG. 4 is a chart showing example apparent water content measurements taken at various humidity levels over time.

FIG. 4 shows an example measurement pattern corresponding to a sample material test performed in this manner. The sample material shown in FIG. 4 is a milk powder with its weight being measured (corresponding to the apparent water content vertical axis) at various ambient humidity levels. For the first about eight hours of testing (i.e., until about 480 minutes), the ambient humidity is held constant at a first level (e.g., about 80%). The ambient humidity is held constant for that period of time to allow the samples to reach vapor pressure equilibrium with the ambient air and to ensure that the apparent water content accordingly remains substantially stable. In this example, the apparent water content was about 8.80 near the end of the eight-hour period.

For the next about four hours (i.e., between about 480 minutes and about 730 minutes), the ambient humidity is held constant at a second level (e.g., about 60%), and the sample reaches vapor pressure equilibrium with the new ambient humidity. Here, the water content at that second ambient humidity is about 9.10. The process is repeated again at about 40% humidity and about 20% humidity to obtain water content readings of about 9.45 and about 9.90, respectively, as shown in the periods from about 730-970 minutes and 970-1200 minutes, respectively. As ambient humidity (and thus vapor pressure) decreases, apparent water content increases because more water is removed from the sample. Going from about 80% humidity to about 20% causes a change in apparent water content of about 1% in this milk powder sample.

The duration of measurements for each ambient humidity level can vary based on the material being tested. For milk powder, for example, about 2-8 hours can be used, but for other materials, different testing durations can be sufficient. The duration of each testing period can be designed to sufficiently allow the material to reach vapor pressure equilibrium at each ambient humidity before moving on to another humidity, as indicated by the values of the weight/water content becoming substantially stable over time. In some embodiments, a set of data points just before a change in humidity (e.g., the last about 12 data points before each change) can be averaged to represent the apparent water content at a particular vapor pressure. In some embodiments, sets of data points can be evaluated for their standard deviation, and data with a standard error of estimate exceeding a threshold value (e.g., a standard error of estimate larger than 0.05) can be discarded and retested. Additionally, although four humidity levels are tested in the process charted in FIG. 4, any number of humidity levels can be used to obtain a set of apparent water content measurements that correspond to different humidity levels over time and to improve the accuracy of the trendline (e.g., 500) determined as discussed below.

While the apparent water content measurements are taken over the time (e.g., as shown in FIG. 4), the vapor pressure at the sample material can also be measured. In standard food or soil processing facilities, the vapor pressure will vary between about 0.5 kPa and about 6.0 kPa, so the apparent water content measurements obtained can be obtained while the corresponding vapor pressures lie within this range. Using these measurements of apparent water content at various humidity levels and the vapor pressures when the sample(s) reaches equilibrium, a mathematical relationship (e.g., a linear relationship) can be established for that sample material, and the relationship can be used to deduce water content at vapor pressures that were not measured in the sample's test. In other words, the relationship between apparent water content and ambient vapor pressure can be used to determine a correction value, as indicated in block 304, and then to modify the apparent water content based on that correction value to a corrected water content that accounts for the ambient humidity at which the apparent water content is measured, as indicated in block 306.

Figure 5:
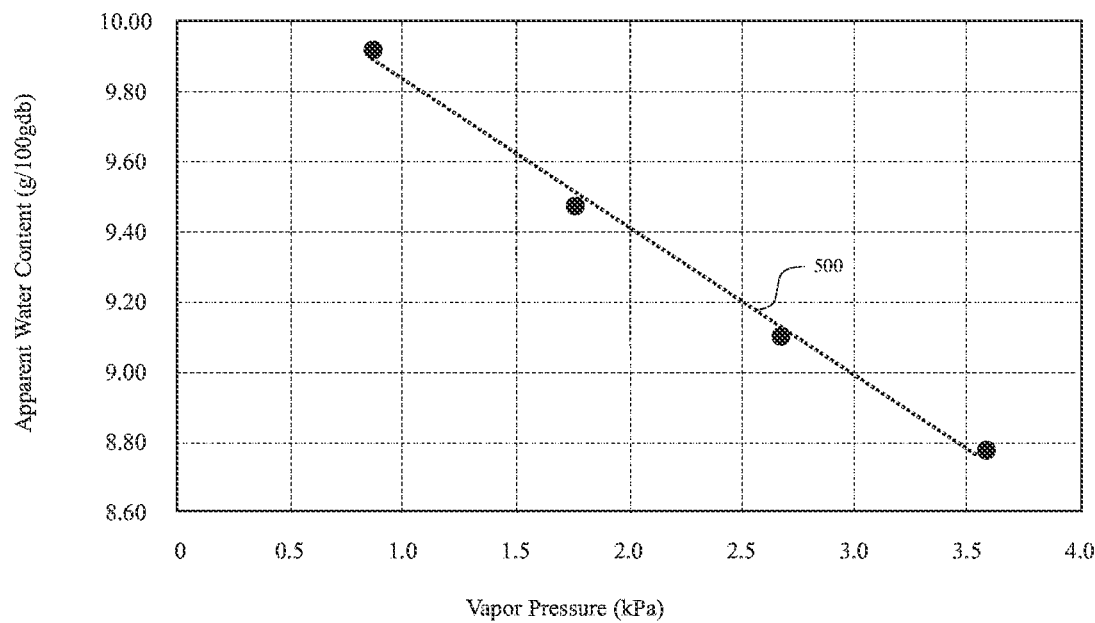
FIG. 5 is a chart showing apparent water content measurements taken at multiple vapor pressures and a trendline of those measurements.

Thus, in accordance with performing block 304, the apparent water content can be plotted relative to the vapor pressure values obtained during the controlled-humidity tests described above in connection with FIG. 4. A sample plot of this kind is shown in FIG. 5. The plot of FIG. 5 shows the apparent water content measurements determined in connection with the process described in connection with FIG. 4 along with the vapor pressure measurements obtained for each apparent water content measurement. A curve-fitting algorithm is used to determine a trendline 500 for the plot, such as a linear regression algorithm. The trendline 500 can be used to determine the correction value or correction factor described above.

For example, in FIG. 5, the trendline 500 has a slope of about −0.42 percent/kPa, so if laboratory vapor pressures fluctuated by ~2 kPa over time (such as between summer and winter conditions), the total uncertainty in the resulting water content measurement would be about 0.84%. For most applications, that amount of variation in the water content measurement is unacceptable, so correcting apparent water content relative to vapor pressure can be invaluable in these testing environments. Additionally, if the drying chamber is permitted to increase its vapor pressure while drying, as is likely when many samples are simultaneously evaporating while being tested, error would increase even further.

After performing the processes described above in connection with FIGS. 4 and 5 for many materials and products, a database of trendline slope information (e.g., slopes of each material's trendline 500) and standard deviation values (e.g., of data sets used to obtain the points shown in FIG. 5) can be generated. Table 1 below shows sample information for various types of soil samples. As expected, apparent water content in high-clay soil such as Palouse B changes significantly as vapor pressure changes, as indicated by the large-magnitude slope value, and apparent water content in dry soil such as vantage sand changes much less significantly (nearly an order of magnitude more slowly) as vapor pressure changes.

TABLE 1

| Material Name | Slope | Std. Dev. |
| --- | --- | --- |
| Palouse A | −0.10562 | 0.001077 |
| Palouse B | −0.22563 | 0.00047 |
| Royal SL | −0.10479 | 0.003708 |
| Vantage Sand | −0.02705 | 0.000613 |

Table 2 below shows sample information for various types of food samples.

TABLE 2

| Material Name | Slope | Std. Dev. |
| --- | --- | --- |
| Jerky | −0.68218 | 0.003133 |
| Carryouts | −0.48377 | 0.003973 |
| Black Pepper | −0.47995 | 0.002883 |
| Salmon | −0.46756 | 0.007256 |
| Milk Powder 1 | −0.42056 | 0.004968 |
| Milk Powder 2 | −0.4197 | 0.005333 |
| Corn Meal | −0.40953 | 0.013114 |
| Flour | −0.40339 | 0.008588 |
| Red Pepper | −0.40329 | 0.026525 |
| Allspice | −0.39062 | 0.001973 |
| House Jerky | −0.37538 | 0.003995 |
| Oregano | −0.35533 | 0.007483 |
| Brown Rice | −0.33938 | 0.000992 |
| Cinnamon | −0.33398 | 0.017618 |
| Chocolate Mix | −0.32339 | 0.002222 |
| AIPC Plain Pasta | −0.30739 | 0.00386 |
| Oberto Jerky | −0.29721 | 0.002721 |
| Popems 1 | −0.29712 | 0.000479 |
| Popems 2 | −0.2911 | 0.015486 |
| Protein Powder | −0.28646 | 0.000817 |
| Kibble | −0.26176 | 0.000951 |
| Iams | −0.2483 | 0.000406 |
| Corn Chips | −0.24099 | 0.003944 |
| Bread Crumbs | −0.23589 | 0.007181 |
| Sausage | −0.21893 | 0.003857 |
| Abbots Formula | −0.17105 | 0.004262 |
| Coffee | −0.16737 | 0.008053 |
| Oberto Sausage | −0.16032 | 0.004269 |
| C&H Brown Sugar | −0.06472 | 0.00189 |
| Salt | −0.00247 | 0.001078 |
| Sugar | −0.00164 | 0.000737 |

The values in the database can be accessed to obtain a correction value that represents a change in apparent water content relative to the testing environment vapor pressure (e.g., the slopes shown in Table 1 or Table 2). Thus, in some embodiments, performance of block 304 can include identifying the sample material being tested in block 302 and finding a correction value for that material in a database (e.g., in a table such as Table 1 or Table 2 above).

Furthermore, as shown in Table 2, salt and sugar have almost no vapor pressure effect, since they are crystalline and hold almost no water until they approach their deliquescence point. Other patterns can also be found in the data, such as, for example, a pattern that samples that are high in carbohydrates have a slope relationship of about −0.4 percent/kPa. Accordingly, in some embodiments, performance of block 304 can include identifying a sample material being tested in block 302 (e.g., receiving user input the identifies the sample material or using a sensor (e.g., an image sensor or spectrometer) to determine the identity of the sample material) and (optionally) determining whether that sample material has a correction value in a database. If the sample material does not have a correction value in the database, the action can include determining a physical or chemical property of the sample material and finding a correction value for a second material having a substantially similar or identical physical or chemical property in the database. Then the correction value for the second material can be used as the correction value of the sample material.

For instance, as indicated above, if salt was the sample material, and if salt had not been analyzed and entered to the database of Table 2, block 304 could include determining that salt is crystalline (or has other properties similar to sugar), finding another material in the database with substantially similar properties (e.g., sugar since it is also crystalline), and using the predetermined correction value (i.e., the slope) of the sugar product as the correction value of the salt. Thus, water content correction can be effected by using correction values for materials that are similar to samples in order to avoid having to go through the steps described in connection with FIGS. 4 and 5 for every material being tested. If no sufficiently similar materials have correction values already determined, performance of block 304 can include performing the tests of FIGS. 4 and 5 and using the results to obtain the correction value (i.e., slope of trendline 500) for the sample material.

Referring again to FIG. 3, once the correction value is obtained, the apparent water content can be modified, changed, and corrected into a corrected or modified water content measurement based on the ambient vapor pressure where the apparent water content was measured, as indicated in block 306. Thus, the corrected water content can be determined by:

$$w = w_a - \alpha(e_a - e_{std}), \quad \text{(Equation 4)}$$

wherein w is the corrected water content, $w_a$ is the apparent water content measured, $\alpha$ is the slope from the database, tables, or figures described above (including the sign), $e_a$ is the vapor pressure of the oven air or other drying chamber's air, and $e_{std}$ is the vapor pressure that is chosen as a "standard value."

If the units of w are g/100 g (or percent), then $\alpha$ will be in percent/kPa. If w is in g/g, then $\alpha$ can be converted accordingly. For small changes near zero water content, dry or wet-basis water content can be used. The "standard value" vapor pressure may be chosen as 0, or a typical laboratory condition can be used based on user preferences and past history (e.g., 1 kPa). A non-zero "standard value" vapor pressure can be optionally used to artificially modify the corrected water content to imitate values measured by the user in the past. For example, if a user has used uncorrected water content measurements historically and accordingly expects to find results within a range of 0.02 to 0.04, but corrected water content measurements cause proper results to lie within a range of 0.01 to 0.03, the standard value can be used to increase the corrected water content to increase by 0.01 so that the user can continue to use their prior testing thresholds without interruption, even after the method 300 is employed.

As discussed above, in some embodiments, input can be provided to a computing device regarding the type or material of the sample being tested and the corresponding α value. In some cases, the a value is estimated based on the general type of material being tested (crystalline, high protein, carbohydrate, etc.).

In one example embodiment, material samples can be placed in an instrument such as an oven (e.g., 102) that is configured to hold and test multiple samples simultaneously. The instrument can have a plurality of independent testing chambers or testing cavities in which different samples can be positioned. The instrument can be connected to a computing device or can be integrated with a computing device (e.g., 110). Via a computer network (e.g., 112) or an input device of the instrument or the computing device, the system can determine the type of product loaded into each sample location in the instrument, as well as the tare and sample weights of the samples. Throughout the measurement, the instrument can circulate ambient air past a vapor pressure (or humidity and temperature) sensor and over the samples being dried. The vapor pressure of the ambient air can be reported to the computing device along with the final dry weight of each sample. The computing device can use the starting and ending weights and the tare weight of each sample to compute an apparent water content. Then, the "alpha" value for the product in each sample location can be accessed in a database (e.g., data store 124), and a corrected water content can be determined from the apparent water content as described above in connection with FIG. 3.

Figure 6:
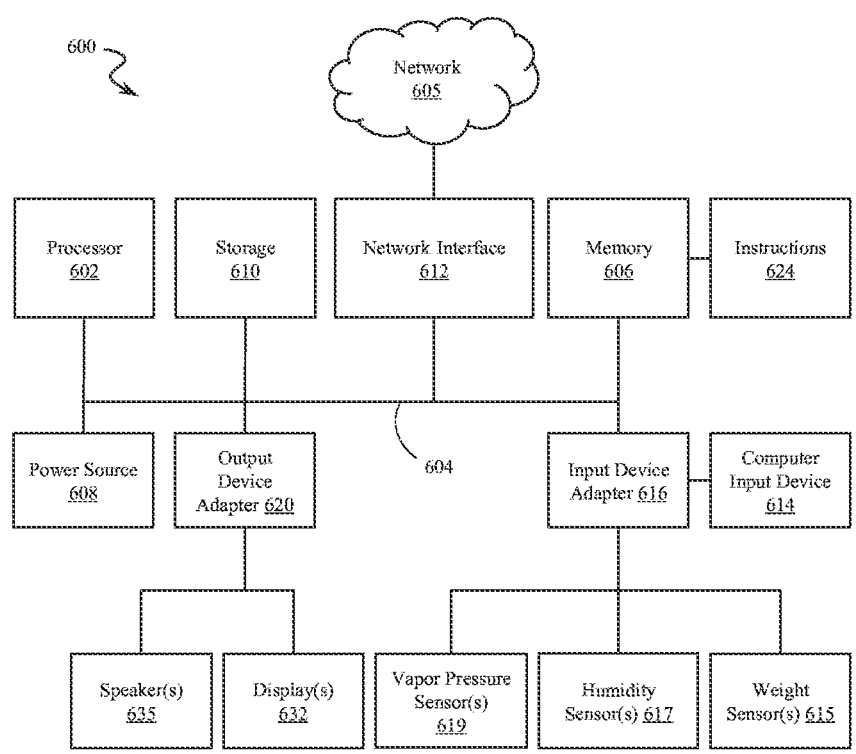
FIG. 6 is a block diagram of a computing system according to the present disclosure.

FIG. 6 is a block diagram showing elements of a computing system 600 that can be used in embodiments of the computing devices discloses herein (e.g., computing device 110). Alternatively, the computing system 600 can be a separate system embodied in a remote device connectable to the computing devices disclosed herein. The computing system 600 can be embodied as a personal computer, a server, a portable computing device, a set of computing devices, similar devices, and combinations thereof.

Accordingly, FIG. 6 is a block diagram of a computer system 600 or computing device according to an embodiment of the present disclosure. In various examples, the computer system 600 can include various sets and subsets of the components shown in FIG. 6. Thus, FIG. 6 shows a variety of components that can be included in various combinations and subsets based on the operations and functions performed by the system 600 in different embodiments. It is noted that, when described or recited herein, the use of the articles such as "a" or "an" is not considered to be limiting to only one, but instead is intended to mean one or more unless otherwise specifically noted herein.

The computer system 600 can include a central processing unit (CPU) or processor 602 connected via a bus 604 for electrical communication to a memory device 606, a power source 608, an electronic storage device 610, a network interface 612, an input device adapter 616, and an output device adapter 620. For example, one or more of these components can be connected to each other via a substrate (e.g., a printed circuit board or other substrate) supporting the bus 604 and other electrical connectors providing electrical communication between the components. The bus 604 can include a communication mechanism (e.g., wires, traces, antennae, etc.) for communicating information between parts of the system 600.

The processor 602 can be a microprocessor, central processing unit, or a similar device configured to receive and execute a set of instructions 624 stored by the memory 606. The memory 606 can be referred to as main memory, such as random access memory (RAM) or another dynamic electronic storage device for storing information and instructions to be executed by the processor 602. The memory 606 can also be used for storing temporary variables or other intermediate information during execution of instructions executed by the processor 602. The storage device 610 can include read-only memory (ROM) or another type of static storage device coupled to the bus 604 for storing static or long-term (i.e., non-dynamic) information and instructions for the processor 602. For example, the storage device 610 can include a magnetic or optical disk (e.g., hard disk drive (HDD)), a solid state memory (e.g., a solid state disk (SSD)), or a comparable device. The power source 608 can include a power supply capable of providing power to the processor 602 and other components connected to the bus 604, such as a connection to an electrical utility grid or a battery system of an autonomous device (e.g., 100).

The instructions 624 can include information for executing processes and methods using components of the system 600 and other components connected to the system 600. Such processes and methods can include, for example, the methods described elsewhere herein, such as, for example, methods described in connection with FIGS. 1-5.

The network interface 612 can include an adapter for connecting the system 600 to an external device via a wired or wireless connection. For example, the network interface 612 can provide a connection to a computer network 605 such as a cellular network, the Internet, a local area network (LAN), network 112, a separate device capable of wireless communication with the network interface 612 (e.g., data store 124 or sensors 106, 107, 108 via communication paths 114, 115, 116, 120, 121, or 122), other external devices or network locations, and combinations thereof. In one example embodiment, the network interface 612 is a wireless networking adapter configured to connect via WI-FI, BLUETOOTH®, BLUETOOTH LOW ENERGY (BLE), long-term evolution (LTE), 5G, a mesh network, or a related wireless communications protocol to another device having interface capability using the same protocol. In some embodiments, a network device or set of network devices in the network 605 can be considered part of the system 600. In some cases, a network device can be considered connected to, but not a part of, the system 600.

The input device adapter 616 can be configured to provide the system 600 with connectivity to various input devices such as, for example, a computer input device 614 (e.g., keyboard or mouse), weight sensors 615 (e.g., scale 108), humidity sensors 617 (e.g., sensor 107), vapor pressure sensors 619 (e.g., sensor 106), one or more other sensors, related devices, and combinations thereof.

The output device adapter 620 can be configured to provide the system 600 with the ability to output information to a user, such as by providing visual output using one or more displays 632 and by providing audible output using one or more speakers 635. The processor 602 can be configured to control the output device adapter 620 to provide information to a user via the output devices connected to the adapter 620.

The instructions 624 can include electronic instructions that, when executed by the processor 602, can perform methods and processes as described in further detail elsewhere herein. The instructions 624 can be stored or encoded on a non-transitory computer readable medium, and the instructions 624, when executed by a computing device such as, for example, processor 602, cause the computing device to perform methods and processes as described in further detail elsewhere herein. See, e.g., FIG. 3.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A system for determining water content of a product, the system comprising:

a drying device including a drying chamber to dry a sample of a product;
a vapor pressure sensor to measure a vapor pressure in air at the drying device;
a weighing device to measure weight of the product in the drying chamber; and
a computing device including:
a processor;
a memory device having instructions encoded thereon which, when executed by the processor, cause the processor to:
obtain an apparent water content of the sample based on a weight difference of the sample obtained via the weighing device and based on the vapor pressure in air at the drying device obtained via the vapor pressure sensor;
determine a correction value representing a change in apparent water content relative to testing environment vapor pressure; and
modify the apparent water content measurement by applying the correction value to the apparent water content.

2. The system of claim 1, wherein obtaining the apparent water content comprises:
obtaining a first weight of the sample in the drying chamber at a first time using the weighing device;
measuring the vapor pressure in air at the drying device using the vapor pressure sensor;
drying the sample in the drying chamber using the drying device;
obtaining a second weight of the sample in the drying chamber at a second time using the weighing device;
determining a weight difference between the first and second weights of the sample; and
calculating the apparent water content of the sample based on the weight difference and the vapor pressure in air at the drying device.

3. The system of claim 1, wherein the method further comprises:
measuring equilibrated water content values of the sample at multiple relative humidities;
measuring vapor pressures at the multiple relative humidities; and
calculating a mathematical relationship between the equilibrated water content values and the vapor pressures, wherein the correction value comprises a slope of the mathematical relationship.

4. The system of claim 1, wherein applying the correction value to the apparent water content comprises taking a difference between the apparent water content measurement and a product of the correction value and the vapor pressure in air at the drying device.

5. The system of claim 1, wherein the computing device is configured to access a database of correction values comprising a predetermined correction value for the product.

6. The system of claim 1, wherein the computing device is configured to access a database of correction values comprising a second correction value for a second product having a characteristic in common with the product and to use the second correction value as the correction value for the product.

7. The system of claim 1, wherein the sample is a food sample, wherein the drying device is configured to dry the food product.

8. A method for correcting a water content measurement of a product, comprising:
obtaining an apparent water content measurement of a product at an ambient vapor pressure in air at a testing environment;
determining a correction value representing a change in apparent water content relative to testing environment vapor pressure; and
modifying the apparent water content measurement by taking a difference between the apparent water content measurement and a product of the correction value and the ambient vapor pressure.

9. The method of claim 8, wherein the ambient vapor pressure is within a range extending from about 0.5 kPa to about 6.0 kPa.

10. The method of claim 8, wherein obtaining the water content measurement comprises drying the product.

11. The method of claim 10, wherein the testing environment is an oven, wherein drying the product comprises heating the product in the oven, and wherein the testing environment vapor pressure is a vapor pressure in the oven.

12. The method of claim 8, wherein determining the correction value comprises accessing a database of correction values comprising a predetermined correction value for the product.

13. The method of claim 8, wherein determining the correction value comprises accessing a database of correction values comprising a second correction value for a second product having a characteristic in common with the product and using the second correction value for the correction value of the product.

14. The method of claim 8, wherein determining the correction value comprises:
measuring equilibrated water content values of the product at multiple relative humidities in a controlled-humidity instrument; and
calculating a linear relationship between the equilibrated water content values and vapor pressures corresponding to each of the equilibrated water content values, wherein the correction value comprises a slope of the linear relationship.

15. The method of claim 8, further comprising reducing the ambient vapor pressure by a vapor pressure standard value.

16. A non-transitory computer-readable medium comprising instructions encoded thereon which, when executed by a processor, cause the processor to perform a method including:
obtaining an apparent water content measurement of a sample product based on a weight difference of the sample while the sample is dried in a testing environment;
measuring a vapor pressure in the testing environment;
determining a correction value representing a relationship between the apparent water content and the vapor pressure; and
correcting the apparent water content measurement by reducing the apparent water content measurement by a factor dependent upon the correction value and the vapor pressure in the testing environment.

17. The non-transitory computer-readable medium of claim 16, wherein the factor is a product of the correction value and the vapor pressure in the testing environment.

18. The non-transitory computer-readable medium of claim 16, wherein determining the correction value comprises accessing a database of correction values and identifying a correction value correlating to a property the sample product.

19. The non-transitory computer-readable medium of claim 16, wherein the correction value represents a change in apparent water content based on vapor pressure for the sample material.

\* \* \* \* \*